(12) United States Patent
Sekiya et al.

(10) Patent No.: US 12,245,868 B2
(45) Date of Patent: Mar. 11, 2025

(54) JOINT IMAGE UNFOLDING APPARATUS, JOINT IMAGE UNFOLDING METHOD, AND JOINT IMAGE UNFOLDING PROGRAM

(71) Applicant: FUJIFILM Corporation, Tokyo (JP)

(72) Inventors: Ichiro Sekiya, Tokyo (JP); Nobutake Ozeki, Tokyo (JP); Akinobu Hyodo, Tokyo (JP); Hayato Aoki, Tokyo (JP); Kenji Suzuki, Tokyo (JP); Jun Masumoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 537 days.

(21) Appl. No.: 17/460,291

(22) Filed: Aug. 29, 2021

(65) Prior Publication Data
US 2021/0390764 A1    Dec. 16, 2021

Related U.S. Application Data

(63) Continuation of application No. PCT/JP2020/009880, filed on Mar. 6, 2020.

(30) Foreign Application Priority Data

Mar. 22, 2019  (JP) ................... 2019-054896

(51) Int. Cl.
*A61B 5/00* (2006.01)
*G06T 7/00* (2017.01)
(Continued)

(52) U.S. Cl.
CPC .......... *A61B 5/4514* (2013.01); *A61B 5/4528* (2013.01); *A61B 5/4585* (2013.01);
(Continued)

(58) Field of Classification Search
CPC ... A61B 5/4514; A61B 5/4528; A61B 5/4571; A61B 5/4576; A61B 5/458;
(Continued)

(56) References Cited

U.S. PATENT DOCUMENTS 6,560,476 B1   5/2003  Pelletier et al.
10,580,136 B2  3/2020  Itai
(Continued)

FOREIGN PATENT DOCUMENTS

JP   2008043759   2/2008
JP   2018042709   3/2018
JP   2018138071   9/2018

OTHER PUBLICATIONS

Kauffmann, Claude, et al. "Computer-aided method for quantification of cartilage thickness and volume changes using MRI: validation study using a synthetic model." IEEE transactions on Biomedical Engineering 50.8 (2003): 978-988. (Year: 2003).*
(Continued)

*Primary Examiner* — Geoffrey E Summers
(74) *Attorney, Agent, or Firm* — JCIPRNET

(57) ABSTRACT

A joint image unfolding apparatus, a joint image unfolding method, and a non-transitory computer readable recording medium storing a joint image unfolding program are provided to make it possible to check information regarding the entire cartilage in a joint with high accuracy. An image obtaining unit (21) obtains a three-dimensional image of a joint having cartilage. An unfolding unit (23) unfolds the cartilage included in the three-dimensional image with reference to a specific reference axis in the joint to generate an unfolded image.

20 Claims, 16 Drawing Sheets

(51) Int. Cl.
*G06T 7/11* (2017.01)
*G06T 7/62* (2017.01)

(52) U.S. Cl.
CPC .............. *G06T 7/0012* (2013.01); *G06T 7/11* (2017.01); *G06T 7/62* (2017.01); *G06T 2207/10081* (2013.01); *G06T 2207/10088* (2013.01); *G06T 2207/10104* (2013.01); *G06T 2207/30004* (2013.01)

(58) Field of Classification Search
CPC .............. A61B 5/4585; G06T 7/0012; G06T 2207/30004; G06T 7/11; G06T 7/62; G06T 2207/10081; G06T 2207/10088; G06T 2207/10104
See application file for complete search history.

(56) References Cited

U.S. PATENT DOCUMENTS

| | | | |
|---|---|---|---|
| 10,806,392 | B2 | 10/2020 | Itai |
| 2008/0044104 | A1 | 2/2008 | Gering |
| 2018/0070874 | A1* | 3/2018 | Itai ...................... A61B 5/0035 |

OTHER PUBLICATIONS

Cohen, Z. A., et al. "Templates of the cartilage layers of the patellofemoral joint and their use in the assessment of osteoarthritic cartilage damage." Osteoarthritis and Cartilage 11.8 (2003): 569-579. (Year: 2003).*

Siversson, Carl, et al. "Three-dimensional hip cartilage quality assessment of morphology and dGEMRIC by planar maps and automated segmentation." Osteoarthritis and Cartilage 22.10 (2014): 1511-1515. (Year: 2014).*

Kwak, S. D., et al. "Hamstrings and iliotibial band forces affect knee kinematics and contact pattern." Journal of orthopaedic research 18.1 (2000): 101-108. (Year: 2000).*

Kwak, Seung Kyu Daniel. Experimental and mathematical investigation of the human knee: anatomy, kinematics and contact. Columbia University, 1997. (Year: 1997).*

Ryan, Mark. "How to Determine the Length of an Arc." For Dummies, Apr. 13, 2017. <https://www.dummies.com/article/academics-the-arts/math/geometry/how-to-determine-the-length-of-an-arc-2-188034/>. (Year: 2017).*

Matthew J. Kraeutler et al., "Variability in the Clock Face View Description of Femoral Tunnel Placement in ACL Reconstruction Using MRI-Based Bony Models," J Knee Surg, vol. 31, Feb. 2018, pp. 965-969.

"Office Action of Japan Counterpart Application" with English translation thereof, issued on May 10, 2022, p. 1-p. 5.

"International Search Report (Form PCT/ISA/210) of PCT/JP2020/009880," mailed on Apr. 14, 2020, with English translation thereof, pp. 1-5.

"Written Opinion of the International Searching Authority (Form PCT/ISA/237)" of PCT/JP2020/009880, mailed on Apr. 14, 2020, with English translation thereof, pp. 1-8.

Office Action of Japan Counterpart Application, with English translation thereof, issued on Oct. 4, 2022, pp. 1-5.

* cited by examiner

JOINT IMAGE UNFOLDING APPARATUS, JOINT IMAGE UNFOLDING METHOD, AND JOINT IMAGE UNFOLDING PROGRAM

CROSS-REFERENCE TO RELATED APPLICATIONS

This application is a Continuation of PCT International Application No. PCT/JP2020/009880 filed on Mar. 6, 2020, which claims priority under 35 U.S.C § 119(a) to Japanese Patent Application No. 2019-054896 filed on Mar. 22, 2019. Each of the above application(s) is hereby expressly incorporated by reference, in its entirety, into the present application.

BACKGROUND OF THE INVENTION

1. Field of the Invention

The present disclosure relates to a joint image unfolding apparatus, a joint image unfolding method, and a non-transitory computer readable recording medium storing a joint image unfolding program for generating an unfolded image of cartilage in a joint from a three-dimensional image including the joint.

2. Description of the Related Art

With recent advancements in medical apparatuses including CT (computed tomography) apparatuses and MRI (magnetic resonance imaging) apparatuses, high-quality and high-resolution three-dimensional images have been increasingly used in diagnostic imaging. A three-dimensional image is formed of a large number of two-dimensional images and has a large amount of information, and therefore, a doctor may take time to find a desired observation part and make a diagnosis. Accordingly, it is a common practice to recognize an organ of interest and use a method, such as the Maximum Intensity Projection (MIP) method or the Minimum Intensity Projection (MinIP) method, to extract the organ of interest from a three-dimensional image that includes the organ of interest and display the organ of interest as, for example, an MIP image or display the three-dimensional image as a Volume Rendering (VR) image, thereby increasing the visibility of the entire organ or a lesion and making the diagnosis more efficient.

Osteoarthritis is a disease that occurs most commonly in elderly persons. Specifically, gonarthrosis causes a pain in the knee joint and narrows the range of motion of the knee joint, and the person may become unable to walk as the symptom becomes worse. To diagnose such osteoarthritis, cartilage of the knee joint needs to be qualitatively evaluated. Accordingly, various methods for quantifying cartilage of the knee joint using a three-dimensional image have been proposed. For example, JP2018-042709A proposes a method in which the projection direction of a cartilage region extracted from an Mill image is determined, the cartilage region is projected in the determined projection direction to generate a projection image, and a quantitative value of the cartilage region is derived on the projection image. With the method described in JP2018-042709A, a region for quantifying the cartilage region can be appropriately determined, and therefore, a stable result of diagnosis can be obtained for the cartilage. Specifically, when the thickness of the cartilage is derived as a quantitative value, the thickness of the cartilage can be evaluated.

As an image for quantitatively evaluating cartilage of the knee joint, a functional image of an MRI image is publicly known. A T2 map image, which is one type of functional image, is an image that represents a correlation with water in tissue as a signal value. With reference to such a functional image, cartilage of a joint can be quantitatively evaluated.

Further, a method has been proposed in which such a functional image is superimposed on an MRI image, which is not a functional image, and displayed to thereby allow a visual diagnosis of quantitative changes in cartilage. For example, JP2018-138071A proposes a method in which a cartilage region is extracted from an MRI image, the MRI image, which is not a functional image, and a functional image are registered, and a mapping image is generated by mapping the functional image onto the MRI image on the basis of the intermediate position of the cartilage region in the thickness direction and the result of registration. With the method described in JP2018-138071A, a projection image obtained by projecting the mapping image is displayed to evaluate the cartilage.

SUMMARY OF THE INVENTION

A joint includes a curved surface and the method described in JP2018-042709A uses a projection image, and therefore, in a part in which the tangential direction of the curved surface of the joint and the projection direction correspond to each other, an error in quantification of the cartilage region becomes large. For example, as illustrated in FIG. 23, it is assumed that a part in which cartilage 91 is present and a part 93 in which the cartilage 91 is in defect are present side by side in the tangential direction at a specific position on the curved surface of a joint 90. In this case, when a three-dimensional image of the joint 90 is projected in a projection direction 92 parallel to the above-described tangential direction, at the projection position in the projection image, the part in which the cartilage 91 is present and the part 93 in which the cartilage 91 is in defect overlap, and therefore, quantification is performed under the assumption that cartilage is present. In such a case, information regarding the part 93 in which the cartilage 91 is in defect is not reflected to the projection image, and as a result, it is difficult to quantify the cartilage with high accuracy. Further, in the method described in JP2018-138071A, the mapping image is displayed as a projection image. Accordingly, to observe the entire image of the cartilage in the joint, an operation of, for example, rotating the mapping image needs to be performed.

The present disclosure has been made in view of the above-described circumstances, and an object thereof is to make it possible to check information regarding the entire cartilage in a joint with high accuracy.

A joint image unfolding apparatus according to the present disclosure includes: an image obtaining unit that obtains a three-dimensional image of a joint having cartilage; and an unfolding unit that unfolds the cartilage included in the three-dimensional image with reference to a specific reference axis in the joint to generate an unfolded image.

Note that the joint image unfolding apparatus according to the present disclosure may further include a display control unit that displays the unfolded image on a display unit.

Further, the joint image unfolding apparatus according to the present disclosure may further include a reference axis setting unit that sets, on respective side surfaces of the joint, center positions determined on the basis of an anatomical characteristic of the joint and sets an axis that connects the center positions as the reference axis.

Further, in the joint image unfolding apparatus according to the present disclosure, the unfolding unit may set an anatomical axis that passes through a center position of the reference axis and a reference point set on a side opposite to a joint surface across the center position of the reference axis and generate the unfolded image with reference to a plane passing though the reference axis and the anatomical axis.

Further, the joint image unfolding apparatus according to the present disclosure may further include a quantification unit that derives a quantitative value of the cartilage on the unfolded image.

Further, in the joint image unfolding apparatus according to the present disclosure, the quantification unit may derive the quantitative value for a region of interest on the unfolded image.

Further, in the joint image unfolding apparatus according to the present disclosure, the unfolding unit may set the region of interest on the basis of a contour that defines a region in which the cartilage is to be present in the joint.

The "contour that defines a region in which the cartilage is to be present" means a contour that defines not a region in which the cartilage is actually present in the joint but a region in which the cartilage is to be anatomically present in the joint.

For example, in the femur, a contour of a region in which cartilage is to be present in the joint is included as a projecting part on the joint surface. Accordingly, in the femur, this projecting part can be regarded as the "contour that defines a region in which cartilage is to be present".

Further, in the joint image unfolding apparatus according to the present disclosure, the quantification unit may derive a cover ratio of the cartilage in the region of interest as the quantitative value.

Further, in the joint image unfolding apparatus according to the present disclosure, the quantification unit may derive a defect area of the cartilage in the region of interest as the quantitative value.

Further, in the joint image unfolding apparatus according to the present disclosure, the quantification unit may derive a representative value of a thickness of the cartilage at each position in the region of interest as the quantitative value.

Further, in the joint image unfolding apparatus according to the present disclosure, the quantification unit may derive a thickness of the cartilage at each position in the region of interest as the quantitative value.

Further, in the joint image unfolding apparatus according to the present disclosure, the quantification unit may generate a thickness map of the cartilage in the region of interest.

Further, the joint image unfolding apparatus according to the present disclosure may further include a display control unit that displays the thickness map on a display unit.

Further, in the joint image unfolding apparatus according to the present disclosure, the quantification unit may derive the quantitative value only for a region in which a thickness of the cartilage in the region of interest is greater than or equal to a predetermined threshold value.

Further, in the joint image unfolding apparatus according to the present disclosure, the quantification unit may divide the region of interest on the unfolded image into regions and derive the quantitative value for each of the regions obtained as a result of division.

Further, in the joint image unfolding apparatus according to the present disclosure, in a case where a result of deriving another quantitative value derived from another three-dimensional image of a subject the same as a subject for which the three-dimensional image is obtained is present, the other three-dimensional image being captured at a different time from a time when the three-dimensional image is captured, the quantification unit may set the region of interest at a position the same as a position of a region of interest for which the other quantitative value is derived.

Further, in the joint image unfolding apparatus according to the present disclosure, the quantification unit may derive an area of the cartilage on the unfolded image as the quantitative value.

Further, in the joint image unfolding apparatus according to the present disclosure, the quantification unit may derive a volume of the cartilage on the unfolded image as the quantitative value.

Further, in the joint image unfolding apparatus according to the present disclosure, in a case where another unfolded image generated from another three-dimensional image of a subject the same as a subject for which the three-dimensional image is obtained is present, the other three-dimensional image being captured at a different time from a time when the three-dimensional image is captured, the unfolding unit may generate the unfolded image with reference to the reference axis the same as a reference axis with reference to which the other unfolded image is generated.

Further, the joint image unfolding apparatus according to the present disclosure may further include a mapping unit that generates a mapping image obtained by mapping a functional image of the joint onto the unfolded image.

The "functional image" is an image having a signal value corresponding to, for example, the amount or correlation of a substance, such as water or collagen, contained in the joint of the subject. Specifically, for example, a T1 map, a T2 map, a T2* map, a T1ρ map, or CEST (Chemical Exchange Saturation Transfer) image obtained by MRI can be used as the functional image.

Further, the joint image unfolding apparatus according to the present disclosure may further include a display control unit that displays the mapping image on a display unit.

Further, in the joint image unfolding apparatus according to the present disclosure, the joint may be a knee joint, an elbow joint, a hip joint, a shoulder joint, or an intervertebral joint.

A joint image unfolding method according to the present disclosure includes: obtaining a three-dimensional image of a joint having cartilage; and unfolding the cartilage included in the three-dimensional image with reference to a specific reference axis in the joint to generate an unfolded image.

Note that the joint image unfolding method according to the present disclosure may be provided as a program, stored in a non-transitory computer readable recording medium, to be executed by a computer.

Another joint image unfolding apparatus according to the present disclosure includes:

a memory that stores an instruction to be executed by a computer; and a processor configured to execute the stored instruction, in which the processor performs a process of obtaining a three-dimensional image of a joint having cartilage, and unfolding the cartilage included in the three-dimensional image with reference to a specific reference axis in the joint to generate an unfolded image.

According to the present disclosure, it is possible to check information regarding cartilage on a surface of a joint with high accuracy. Further, it is possible to easily check the condition of cartilage on the entire surface of a joint by viewing an unfolded image without rotating the unfolded image.

DESCRIPTION OF THE PREFERRED EMBODIMENTS

Figure 1:
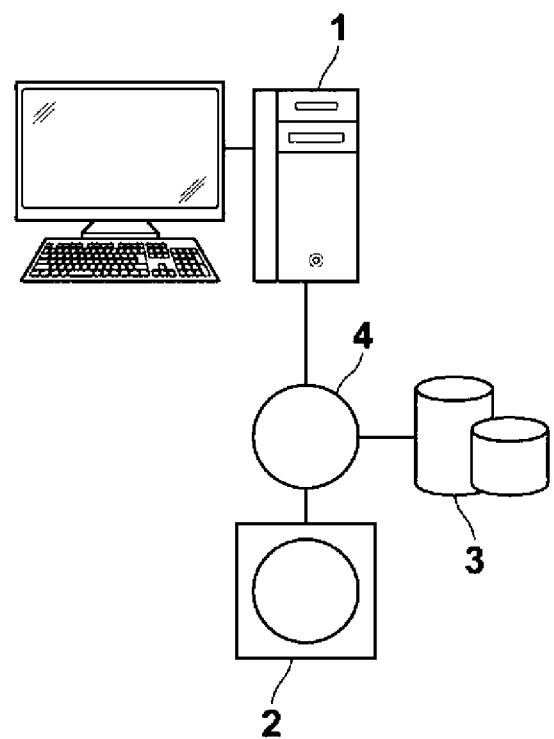
FIG. 1 is a hardware configuration diagram schematically illustrating a diagnosis support system to which a joint image unfolding apparatus according to a first embodiment of the present disclosure is applied.

Hereinafter, embodiments of the present disclosure will be described with reference to the drawings. FIG. 1 is a hardware configuration diagram schematically illustrating a diagnosis support system to which a joint image unfolding apparatus according to a first embodiment of the present disclosure is applied. As illustrated in FIG. 1, in the diagnosis support system, a joint image unfolding apparatus 1 according to this embodiment, a three-dimensional imaging apparatus 2, and an image storage server 3 are connected to each other via a network 4 such that communication is possible.

The three-dimensional imaging apparatus 2 is an apparatus that images a diagnosis target part of a subject to generate a three-dimensional image representing the part, and specifically is, for example, a CT apparatus, an MRI apparatus, or a PET (positron emission tomography) apparatus. The three-dimensional image generated by the three-dimensional imaging apparatus 2 is transmitted to the image storage server 3 and saved in the image storage server 3. This embodiment assumes that the diagnosis target part of a patient who is the subject is the knee joint, the three-dimensional imaging apparatus 2 is an MRI apparatus, and an MRI image of the knee joint of the subject is generated as the three-dimensional image.

The image storage server 3 is a computer that saves and manages various types of data and includes an external mass storage device and database management software. The image storage server 3 communicates with other apparatuses via the network 4, which is a wired or wireless network, to transmit and receive, for example, image data. Specifically, the image storage server 3 obtains various types of data including image data of, for example, a three-dimensional image generated by the three-dimensional imaging apparatus 2 and saves the various types of data in a recording medium, which is, for example, the external mass storage device, to manage the various types of data. The form of storage of image data and communication between apparatuses via the network 4 conform to a protocol, such as DICOM (Digital Imaging and Communication in Medicine).

The joint image unfolding apparatus 1 is configured by installing a joint image unfolding program of the present disclosure in one computer. The computer may be a workstation or a personal computer that is directly operated by a doctor who makes a diagnosis or may be a server computer connected to the workstation or the personal computer via a network. The joint image unfolding program is recorded to a recording medium, such as a DVD (digital versatile disc) or a CD-ROM (compact disk read-only memory), distributed, and installed in the computer from the recording medium. Alternatively, the joint image unfolding program is stored in a storage device of a server computer connected to the network or in a network storage so as to be externally accessible, downloaded to the computer used by the doctor in response to a request, and installed in the computer.

Figure 2:
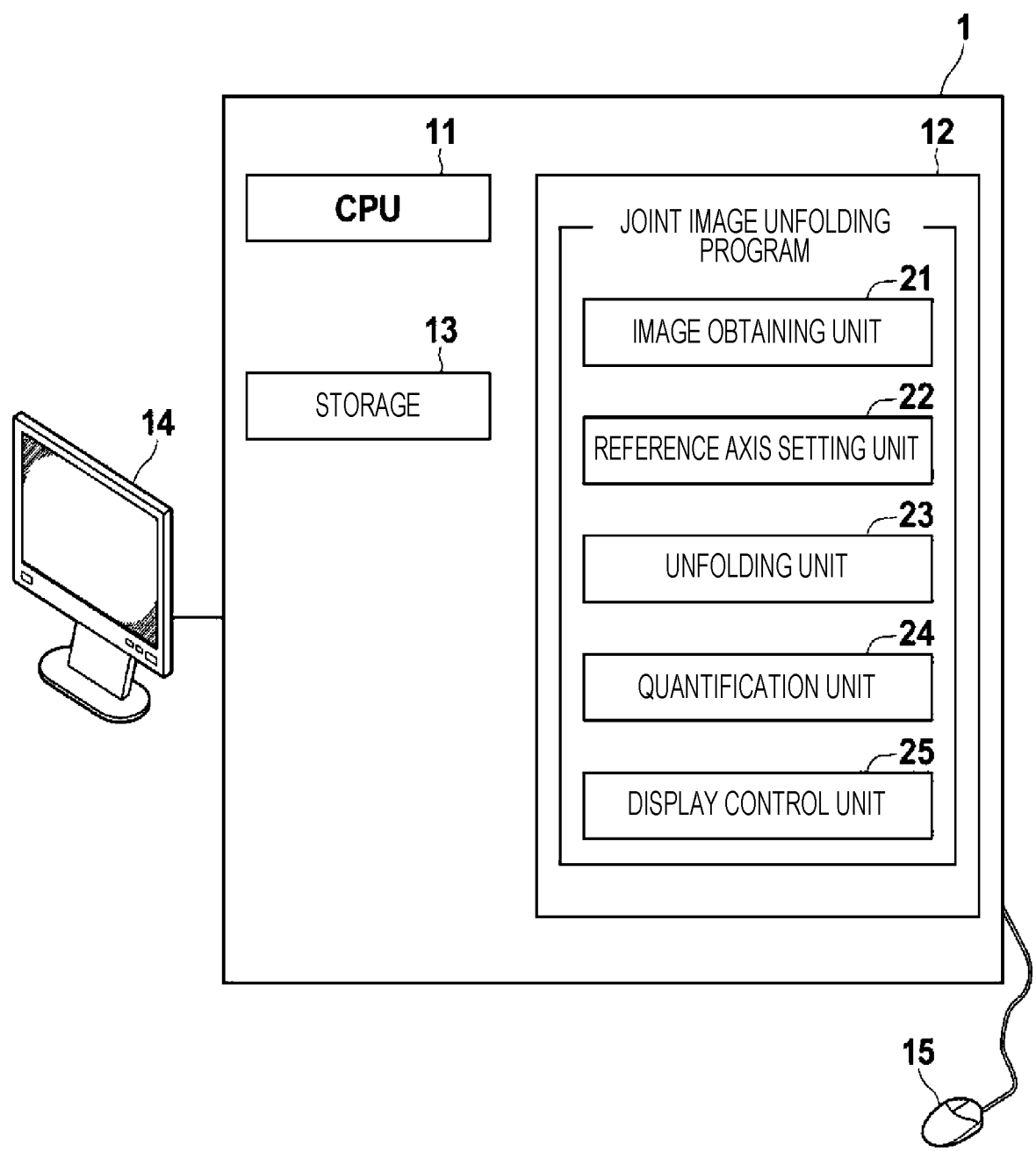
FIG. 2 is a schematic block diagram illustrating a configuration of the joint image unfolding apparatus according to the first embodiment.

FIG. 2 is a diagram schematically illustrating a configuration of the joint image unfolding apparatus according to the first embodiment of the present disclosure implemented by installing the joint image unfolding program in the computer. As illustrated in FIG. 2, the joint image unfolding apparatus 1 includes a CPU (central processing unit) 11, a memory 12, and a storage 13 as in a configuration of a typical workstation. To the joint image unfolding apparatus 1, a display unit 14 and an input unit 15, which includes, for example, a keyboard and a mouse, is connected.

In the storage 13, a three-dimensional image of a subject obtained from the image storage server 3 via the network 4 and various types of information including information necessary for processing are stored. This embodiment assumes that a three-dimensional image G0 of the knee joint of a subject, which is a diagnosis target part, is stored in the storage 13.

In the memory 12, the joint image unfolding program is stored. In this case, the memory 12 is formed of a nonvolatile memory. As processes to be performed by the CPU 11, the joint image unfolding program defines an image obtaining process of obtaining the three-dimensional image G0, a reference axis setting process of setting a reference axis that serves as a reference for generating an unfolded image described below, an unfolding process of unfolding cartilage of the joint included in the three-dimensional image G0 with reference to the reference axis to generate an unfolded image, a quantification process of deriving quantitative values of the cartilage on the unfolded image, and a display control process of displaying a thickness map described below derived as a result of quantification on the display unit 14. Further, the joint image unfolding program may be stored in the storage 13 and temporarily loaded to the memory 12 and executed by the CPU 11. In this case, the memory 12 is formed of a volatile memory.

When the CPU 11 performs these processes in accordance with the program, the computer functions as an image obtaining unit 21, a reference axis setting unit 22, an unfolding unit 23, a quantification unit 24, and a display control unit 25.

Figure 3:
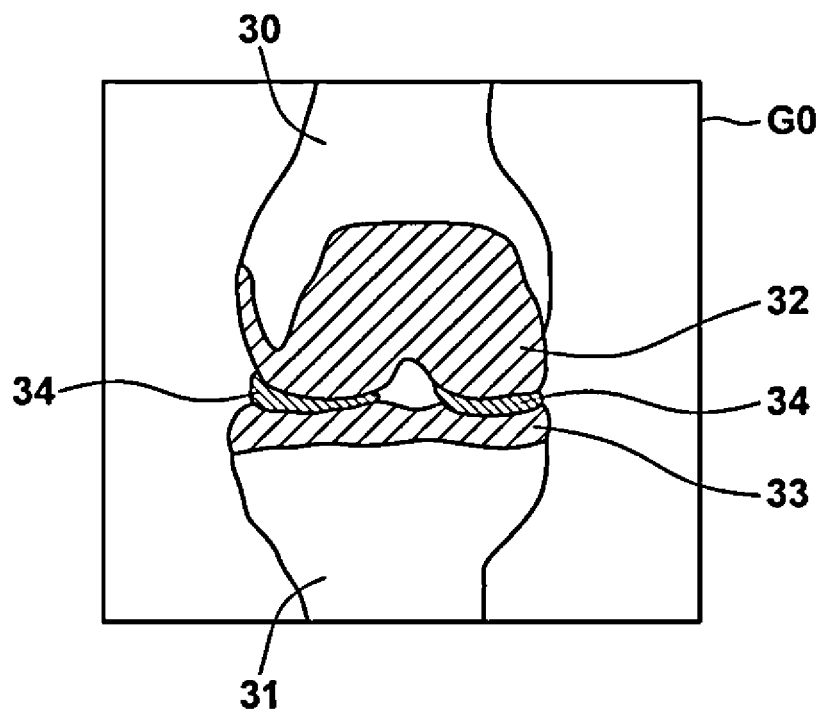
FIG. 3 is a diagram illustrating a three-dimensional image of a knee joint.

The image obtaining unit 21 obtains the three-dimensional image G0 of the knee joint of the subject from the image storage server 3. In a case where the three-dimensional image G0 is already stored in the storage 13, the image obtaining unit 21 may obtain the three-dimensional image G0 from the storage 13. FIG. 3 is a diagram illustrating the three-dimensional image G0 of the knee joint. As illustrated in FIG. 3, the three-dimensional image G0 includes a femur 30 and a tibia 31. In FIG. 3, the patella is omitted for convenience of description. Cartilage 32 is present in a part of the femur 30 facing the tibia 31, and cartilage 33 is present in a part of the tibia 31 facing the femur 30. Between the cartilage 32 and the cartilage 33, menisci 34 are present. In this embodiment, the three-dimensional image G0 is an MRI image, and the range of signal values (voxel values) in the three-dimensional image G0 differs among a bone region, a cartilage region, a meniscus region, and other regions including a muscle region and a fat region. The image obtaining unit 21 extracts a bone region and a cartilage region from the three-dimensional image G0 by performing a threshold value process for the signal values. Specifically, the image obtaining unit 21 extracts a region in which the signal values are within the range of signal values of bones in the three-dimensional image G0 as a bone region. The image obtaining unit 21 extracts a region in which the signal values are within the range of signal values of cartilage in the three-dimensional image G0 as a cartilage region. The bone region includes the femur 30 and the tibia 31, and the cartilage region includes the cartilage 32 and the cartilage 33. In this embodiment, although the image obtaining unit 21 extracts a bone region and a cartilage region from the three-dimensional image G0, this embodiment is not limited to this. Means for extracting a bone region and a cartilage region from the three-dimensional image G0 may be separately provided. This embodiment assumes that the cartilage 32 of the femur 30 is extracted as a cartilage region. To extract a bone region and a cartilage region from the three-dimensional image G0, the threshold value process need not be performed. For example, a classifier that is subjected to machine learning by, for example, deep learning to extract a bone region and a cartilage region from the three-dimensional image G0 may be used.

The reference axis setting unit 22 sets, on respective side surfaces of the joint of the femur 30, center positions determined on the basis of the anatomical characteristics of the joint and sets an axis that connects the center positions as a reference axis. The side surfaces are side surfaces of the joint when viewed from the front of the human body. Setting of the reference axis is described below. The reference axis setting unit 22 first cuts the femur 30 extracted from the three-dimensional image G0 to a predetermined length so as to include the joint. The length needs to be, for example, about 10 cm but is not limited to this. The reference axis setting unit 22 obtains three points of a cut femur 30A at which the femur 30A is in contact with a plane when the femur 30A is placed on the plane with the medial condyle and the lateral condyle down.

Figure 4:
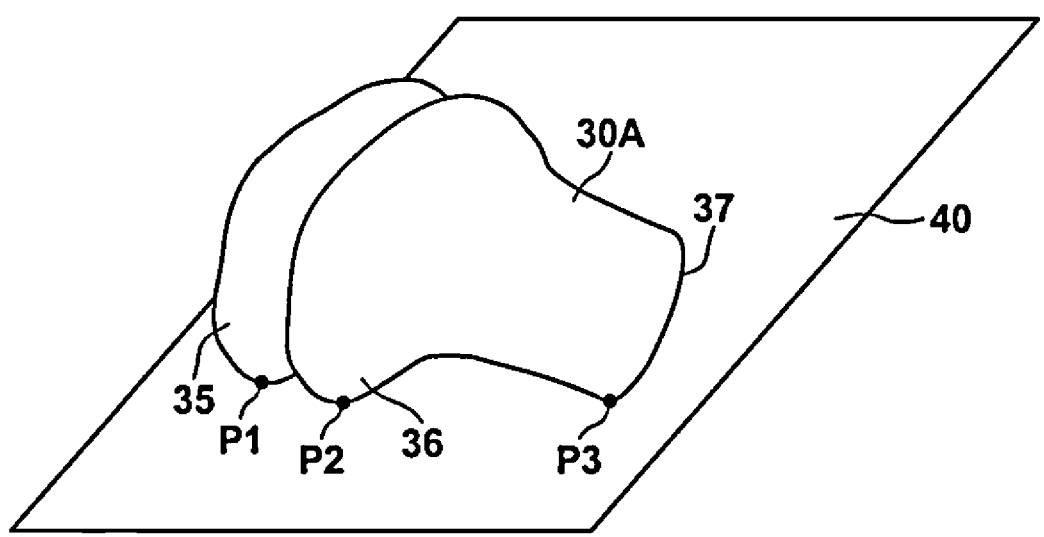
FIG. 4 is a diagram illustrating a state where a cut femur is placed on a plane.

FIG. 4 is a diagram illustrating a state where the cut femur 30A is placed on a plane. As illustrated in FIG. 4, when the femur 30A is placed on a plane 40 with a medial condyle 35 and a lateral condyle 36 down, the femur 30A is in contact with the plane 40 at three points P1 to P3 in the medial condyle 35, the lateral condyle 36, and the periphery of a section 37, respectively.

Figure 5:
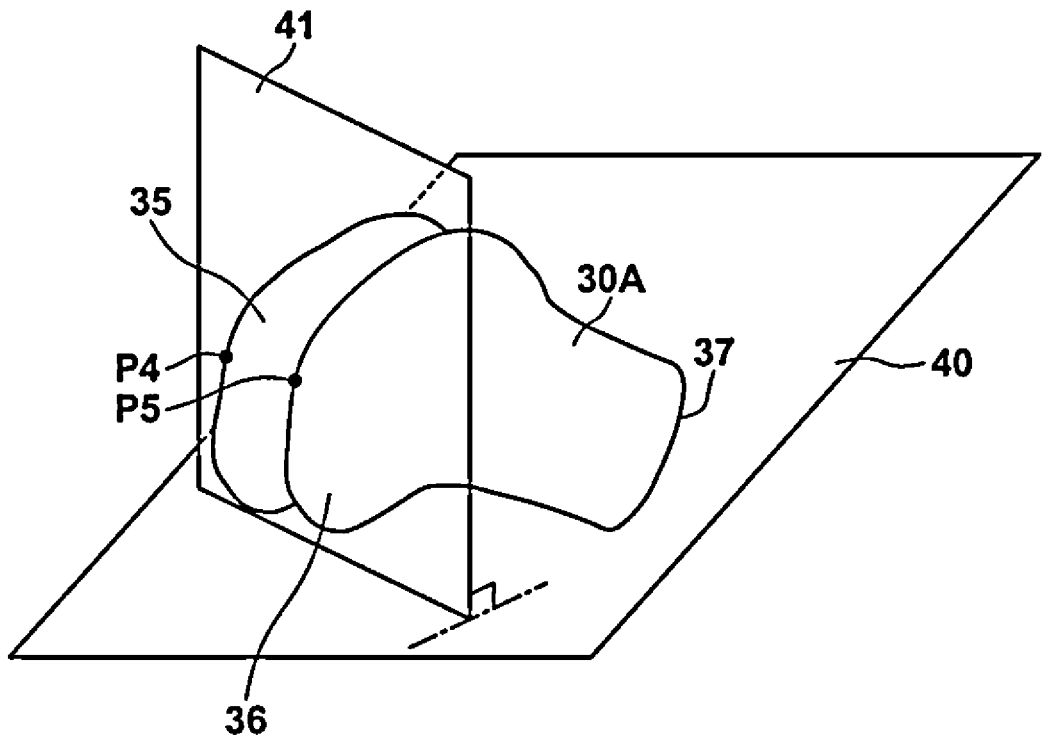
FIG. 5 is a diagram for explaining setting of a reference axis.

Next, as illustrated in FIG. 5, the reference axis setting unit 22 sets, on the joint side of the femur 30A on the plane 40 that passes through the three points P1 to P3, a plane 41 that is orthogonal to the plane 40 and that is in contact with the femur 30A at at least two points. As illustrated in FIG. 5, the plane 41 is perpendicular to the plane 40 and is in contact with the medial condyle 35 and the lateral condyle 36 of the femur 30A at points P4 and P5, respectively.

Figure 6:
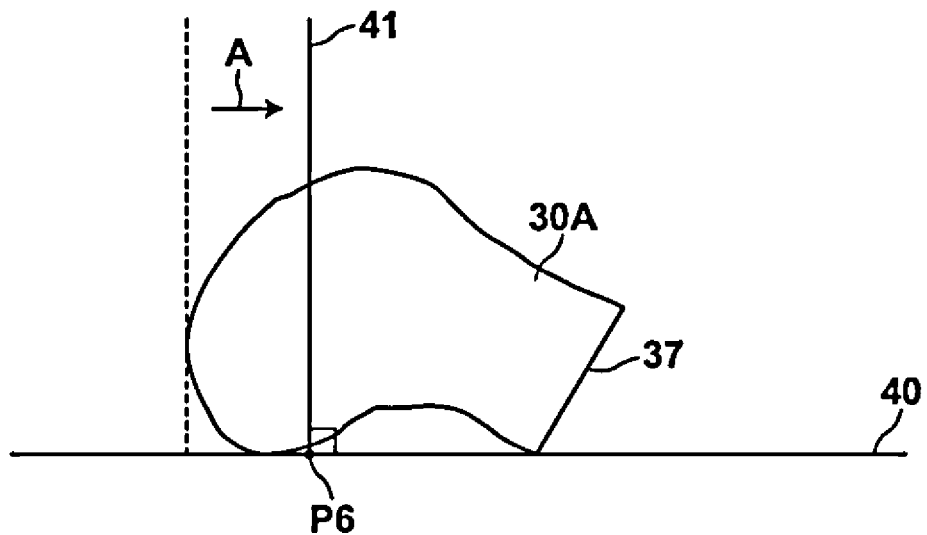
FIG. 6 is a diagram for explaining setting of a reference axis.

As illustrated in FIG. 6, the reference axis setting unit 22 moves the plane 41 in the arrow A direction orthogonal to the plane 41. As illustrated in FIG. 6, the reference axis setting unit 22 obtains a position P6 of the plane 41 at which the plane 41 intersects with the femur 30A along the longest length when the femur 30A is viewed in a direction parallel to the plane 41. A line-of-sight direction in which the femur 30A illustrated in FIG. 6 is viewed is referred to as a first direction, and a line-of-sight direction in which the femur 30A is viewed from the opposite side to the first direction is referred to as a second direction.

Figure 7:
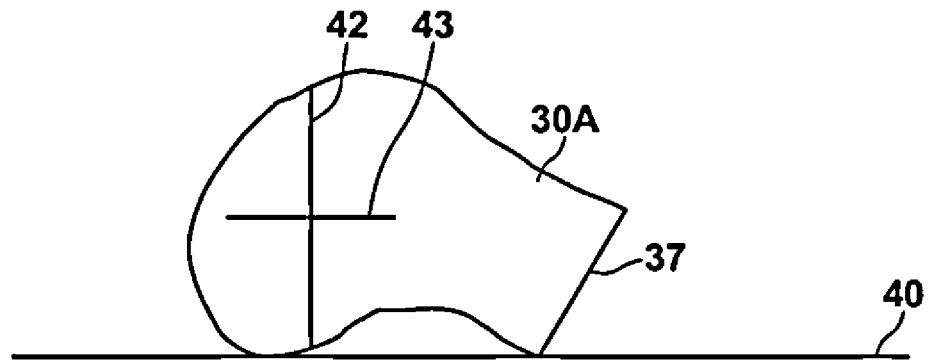
FIG. 7 is a diagram for explaining setting of a reference axis.

When the plane 41 is located at the position P6, the reference axis setting unit 22 sets, as illustrated in FIG. 7, a line segment within a range that intersects with the femur 30A when the femur 30A is viewed in the first direction as a major axis 42 for ellipse fitting described below. The reference axis setting unit 22 sets a minor axis 43 that passes through the center position of the major axis 42 and that has a predetermined length relative to the major axis 42 (for example, 0.8 times the major axis 42).

Figure 8:
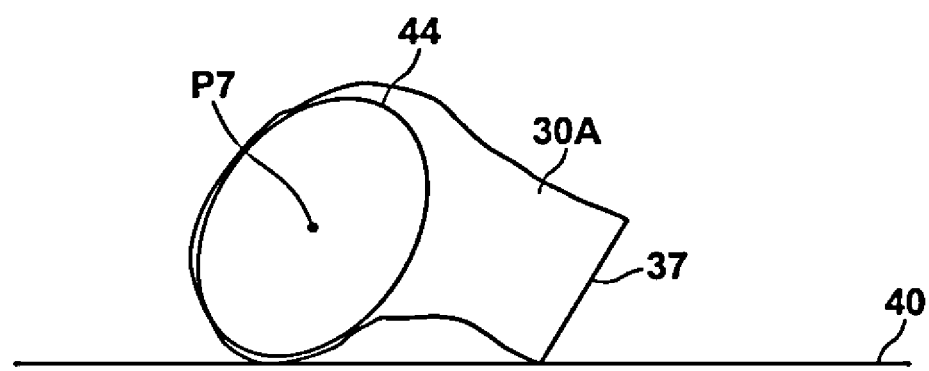
FIG. 8 is a diagram for explaining setting of a reference axis.
Figure 9:
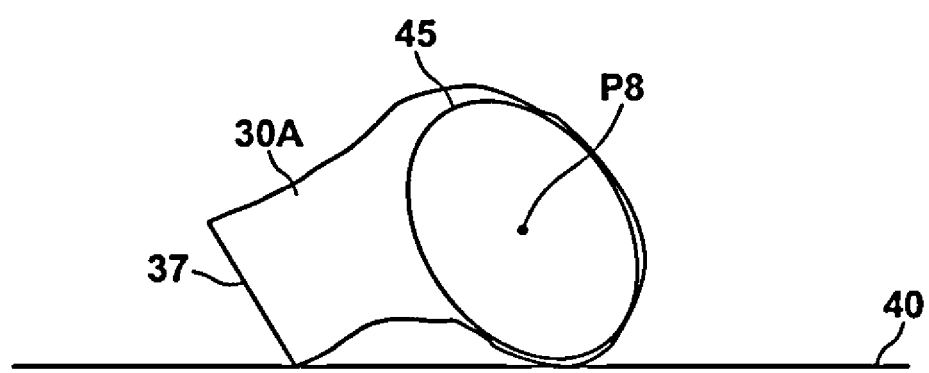
FIG. 9 is a diagram for explaining setting of a reference axis.

As illustrated in FIG. 8, the reference axis setting unit 22 uses an ellipse having the set major axis 42 and minor axis 43 as initial values to perform ellipse fitting for the femur 30A viewed in the first direction. The reference axis setting unit 22 obtains a center position P7 of an ellipse 44 obtained as a result of the fitting. Next, as illustrated in FIG. 9, the reference axis setting unit 22 performs ellipse fitting for the femur 30A when viewed in the second direction opposite to the first direction and obtains a center position P8 of an ellipse 45 obtained as a result of the fitting. The reference axis setting unit 22 sets a straight line that passes through the center positions P7 and P8 as a reference axis 46.

Figure 10:
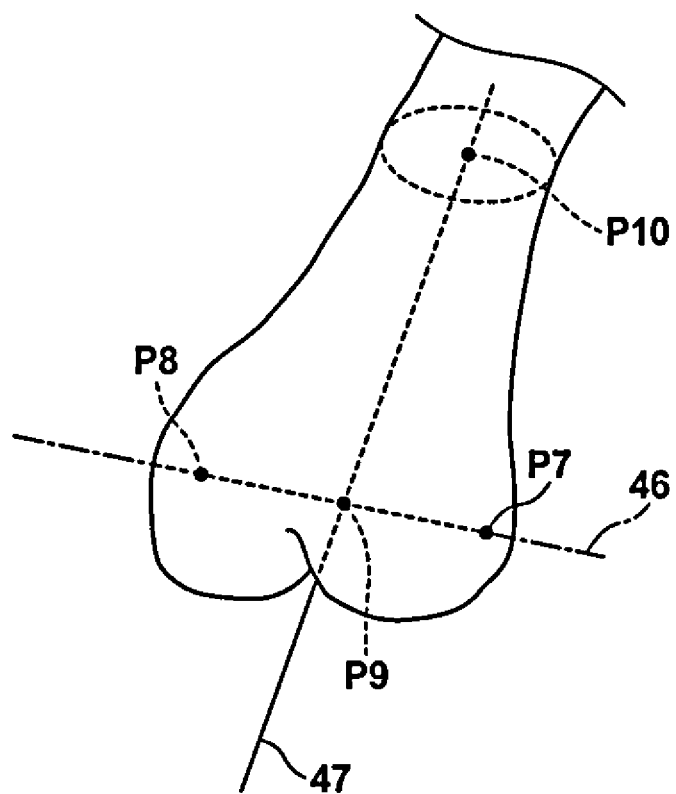
FIG. 10 is a diagram for explaining generation of an unfolded image.
Figure 11:
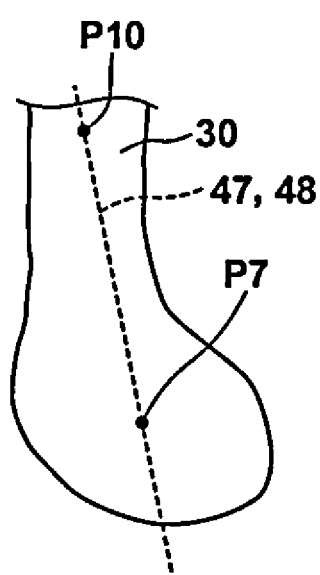
FIG. 11 is a diagram for explaining generation of an unfolded image.

The unfolding unit 23 unfolds cartilage included in the three-dimensional image G0 with reference to the reference axis 46 set by the reference axis setting unit 22 to generate an unfolded image. For this, as illustrated in FIG. 10, the unfolding unit 23 first obtains a center position P9 of the reference axis 46. The center position P9 is the position of the middle point between the center position P7 and the center position P8 on the reference axis 46. The unfolding unit 23 sets as a reference point, a center position P10 of a cross section orthogonal to the femur 30 at a position away from the reference axis 46 by a predetermined distance along the femur 30 on the side opposite to the joint surface. The unfolding unit 23 sets a straight line that passes through the center positions P9 and P10 as an anatomical axis 47. The unfolding unit 23 sets a plane 48 that passes through the reference axis 46 and the anatomical axis 47. FIG. 11 is a diagram of the femur 30, for which the anatomical axis 47 is set, when viewed in the first direction. In FIG. 11, the anatomical axis 47 and the plane 48 correspond to each other.

Figure 12:
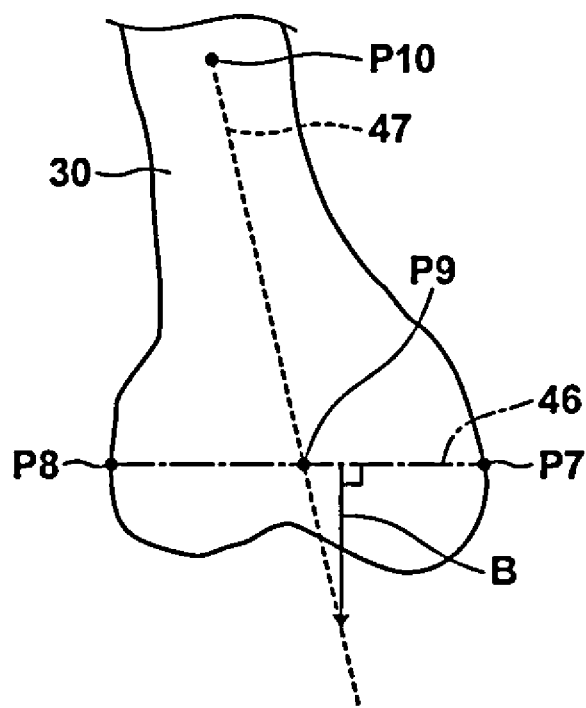
FIG. 12 is a diagram for explaining generation of an unfolded image.

FIG. 12 is a diagram of the femur 30, for which the anatomical axis 47 is set, when viewed in a direction orthogonal to the first and second directions (for example, from the front of the human body). The unfolding unit 23 sets a cross section along the direction (the arrow B direction in FIG. 12) orthogonal to the reference axis 46 on the plane 48 as a reference position for generating an unfolded image. Here, the reference position is a reference position for unfolding cartilage around the reference axis 46, and an angle, with respect to the reference axis 46, corresponding to the reference position is set to 0 degrees.

Figure 13:
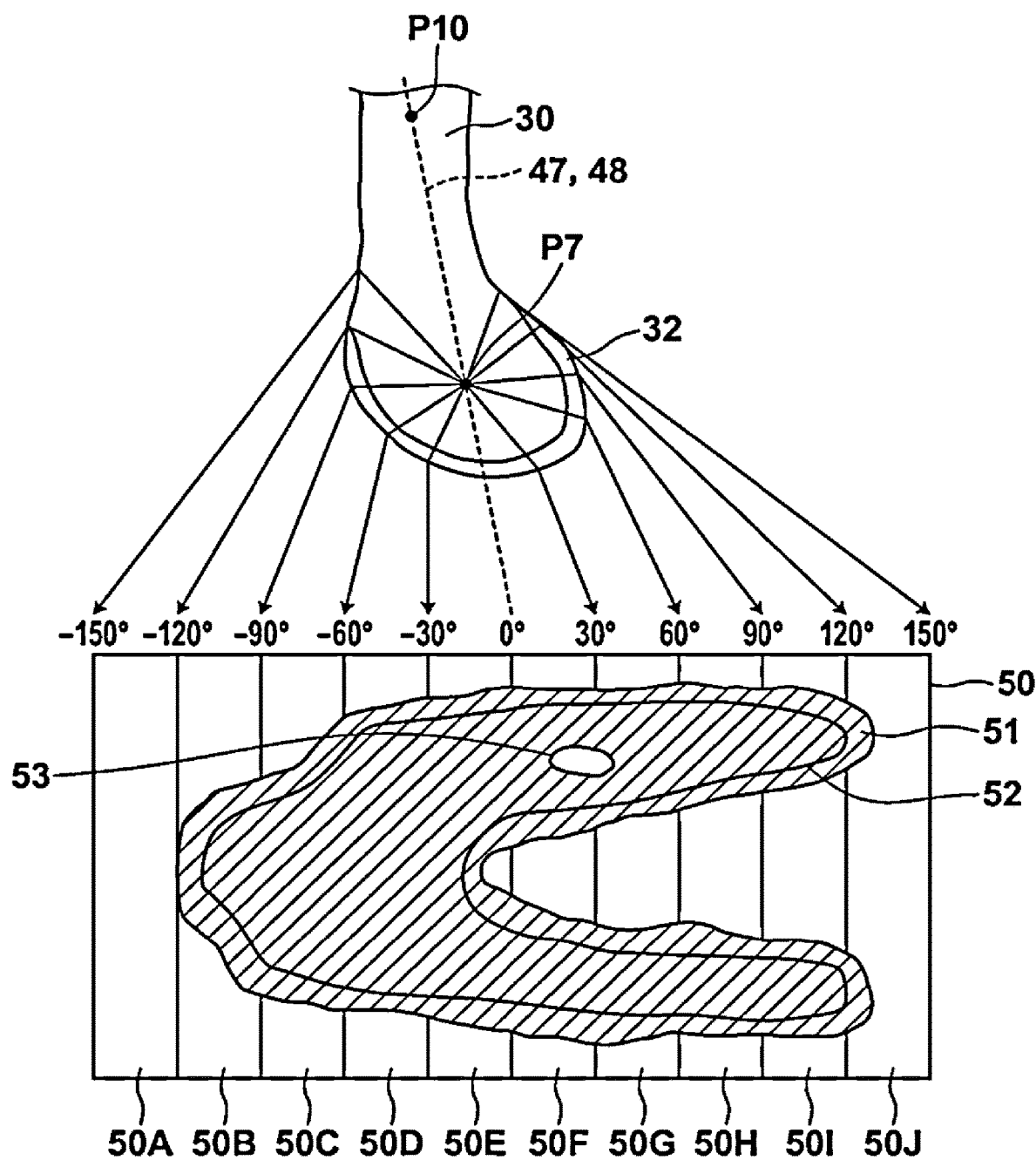
FIG. 13 is a diagram for explaining unfolding of cartilage.
Figure 14:
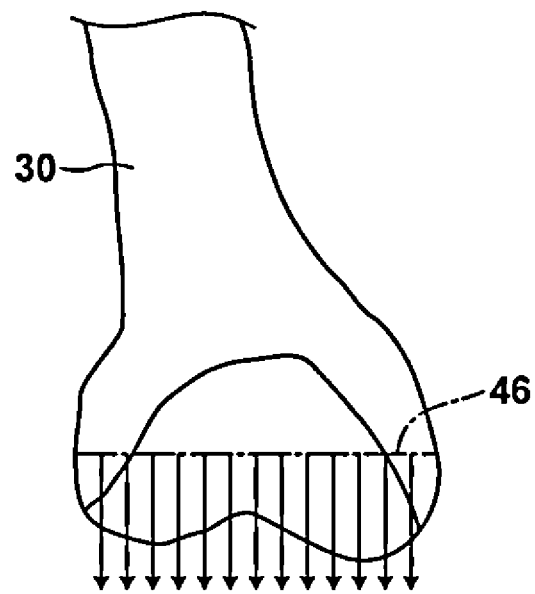
FIG. 14 is a diagram for explaining unfolding of cartilage.

The unfolding unit 23 unfolds the cartilage 32 of the femur 30 with reference to the reference axis 46, that is, around the reference axis 46, while assuming the reference position as 0 degrees to generate an unfolded image. FIG. 13 and FIG. 14 are diagrams for explaining unfolding of the cartilage 32. As illustrated in FIG. 13 and FIG. 14, for each local position on the reference axis 46 and concentrically with the reference axis 46, the unfolding unit 23 unfolds the cartilage 32 of the femur 30 onto a plane to generate a two-dimensional unfolded image 50. The unfolded image 50 includes a cartilage region 51. In FIG. 13, angles with respect to the reference axis 46 are indicated in the unfolded image 50. As described above, 0 degrees is the angle at the reference position with respect to the reference axis 46. In FIG. 14, although a downward arrow is additionally illustrated for each local position on the reference axis 46 for convenience of description, in actuality, the cartilage 32 is unfolded concentrically with the reference axis 46 at intervals of one pixel on the reference axis 46.

The unfolding unit 23 sets a region of interest on the unfolded image 50. In this embodiment, the unfolding unit 23 sets a region corresponding to a subchondral bone region in the joint as a region of interest 52. The subchondral bone region is a region of the joint of the femur 30 in which the joint of the femur 30 and the joint of the tibia 31 rub each other. The peripheral part of the cartilage region 51 in the unfolded image 50 and the joint of the tibia 31 do not rub each other. Therefore, the unfolding unit 23 extracts a region of the cartilage region 51 in the unfolded image 50 except a region that is within a predetermined range from the edge part of the cartilage region 51 as the subchondral bone region and sets the extracted subchondral bone region as the region of interest 52. The unfolding unit 23 divides the unfolded image 50 on the basis of angle ranges. For example, the unfolding unit 23 divides the unfolded image 50 into ten regions, that is, a region 50A corresponding to an angle range of −150 degrees or more and less than −120 degrees, a region 50B corresponding to an angle range of −120 degrees or more and less than −90 degrees, a region 50C corresponding to an angle range of −90 degrees or more and less than −60 degrees, a region 50D corresponding to an angle range of −60 degrees or more and less than −30 degrees, a region 50E corresponding to an angle range of −30 degrees or more and less than 0 degrees, a region 50F corresponding to an angle range of 0 degrees or more and less than 30 degrees, a region 50G corresponding to an angle range of 30 degrees or more and less than 60 degrees, a region 50H corresponding to an angle range of 60 degrees or more and less than 90 degrees, a region 50I corresponding to an angle range of 90 degrees or more and less than 120 degrees, and a region 50J corresponding to an angle range of 120 degrees or more and less than 150 degrees. The region of interest 52 need not be set by the unfolding unit 23 and may be set by the quantification unit 24 described below.

Figure 15:
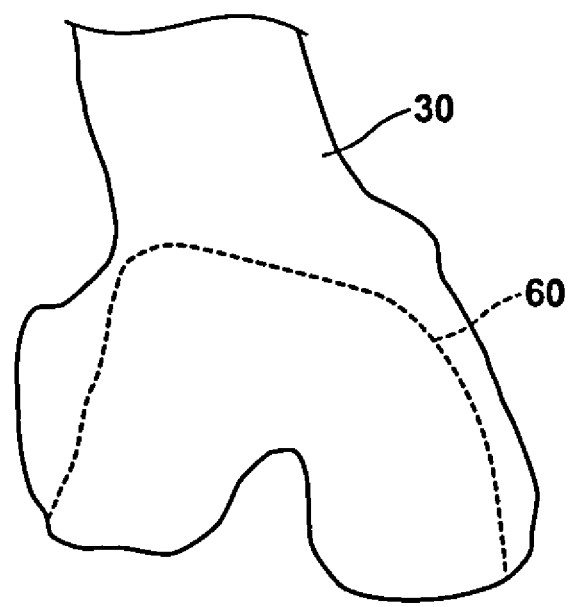
FIG. 15 is a diagram for explaining setting of a region of interest.

In the femur 30, as illustrated in FIG. 15, a contour that defines a region in which cartilage is to be present in the joint is included as a projecting part 60 on the joint surface. In FIG. 15, the projecting part 60 is indicated by a dashed line. The projecting part 60 defines the contour of an area in which cartilage is to be present in the joint. Therefore, the unfolding unit 23 may regard a region surrounded by the projecting part 60 on the joint surface as the cartilage region 51 and set the region of interest 52.

The quantification unit 24 derives quantitative values of the cartilage region 51 on the unfolded image 50. Specifically, the quantification unit 24 derives quantitative values for the region of interest 52 on the unfolded image 50. The quantification unit 24 derives quantitative values for each of the ten regions, that is, the regions 50A to 50J, in the unfolded image 50. The unfolding unit 23 may derive quantitative values for the entire region of interest 52.

First, the quantification unit 24 derives the area of the region of interest 52 and the area of the cartilage region 51 in the region of interest 52 for each of the regions 50A to 50J. In the unfolded image 50, the area of one pixel is known. Therefore, the quantification unit 24 counts the number of pixels in the region of interest 52 and that in the cartilage region 51 for each of the regions 50A to 50J and multiples the counted number of pixels by the area of one pixel to thereby derive the area of the cartilage region 51 and that of the region of interest 52. The area of the cartilage region 51 is one of the quantitative values.

The quantification unit 24 derives the thickness of the cartilage region 51 in each of the regions 50A to 50J as a quantitative value. Here, the position of each pixel in the unfolded image 50 and a corresponding position in the cartilage 32 of the femur 30 in the three-dimensional image G0 can be associated with each other. The quantification unit 24 associates the position of each pixel in the region of interest 52 in the unfolded image 50 with the position of a corresponding pixel in the cartilage 32 of the femur 30 in the three-dimensional image G0. In a normal direction at the position of each pixel in the cartilage 32, the quantification unit 24 derives the number of pixels between the surface of the cartilage 32 and the surface of the bone part of the femur 30. The quantification unit 24 multiples the derived number of pixels by the length of one pixel to thereby derive the thickness of the cartilage region 51.

The quantification unit 24 derives the volume of the cartilage region 51 in each of the regions 50A to 50J as a quantitative value. The quantification unit 24 can derive the volume of the cartilage region 51 by multiplying the area of the cartilage region 51 by the thickness thereof in each of the regions 50A to 50J.

The quantification unit 24 further derives other quantitative values from the area and thickness of the cartilage region 51 in each of the regions 50A to 50J. Specifically, the quantification unit 24 derives the cover ratio of the cartilage region 51 in the region of interest 52, a defect area of the cartilage region 51 in the region of interest 52, and a representative value of the thickness of the cartilage region 51 at each position in the region of interest 52 as quantitative values.

As the cover ratio of the cartilage region 51 in the region of interest 52, the quantification unit 24 derives (the area of the cartilage region 51 in the region of interest 52)/(the area of the region of interest 52) for each of the regions 50A to 50J in the region of interest 52.

As the defect area of the cartilage region 51 in the region of interest 52, the quantification unit 24 derives the area of a region in which the cartilage region 51 is not present for each of the regions 50A to 50J. For example, a region 53 illustrated in FIG. 13 is a region in which cartilage is not present, and therefore, the area of the region 53 in which cartilage is not present in the regions 50F and 50G is the defect area of the cartilage region 51.

As a representative value of the thickness of the cartilage region 51 at each position in the region of interest 52, the quantification unit 24 derives, for example, the average value, intermediate value, minimum value, or maximum value of the thickness of the cartilage region 51 in each of the regions 50A to 50J in the region of interest 52.

Figure 16:
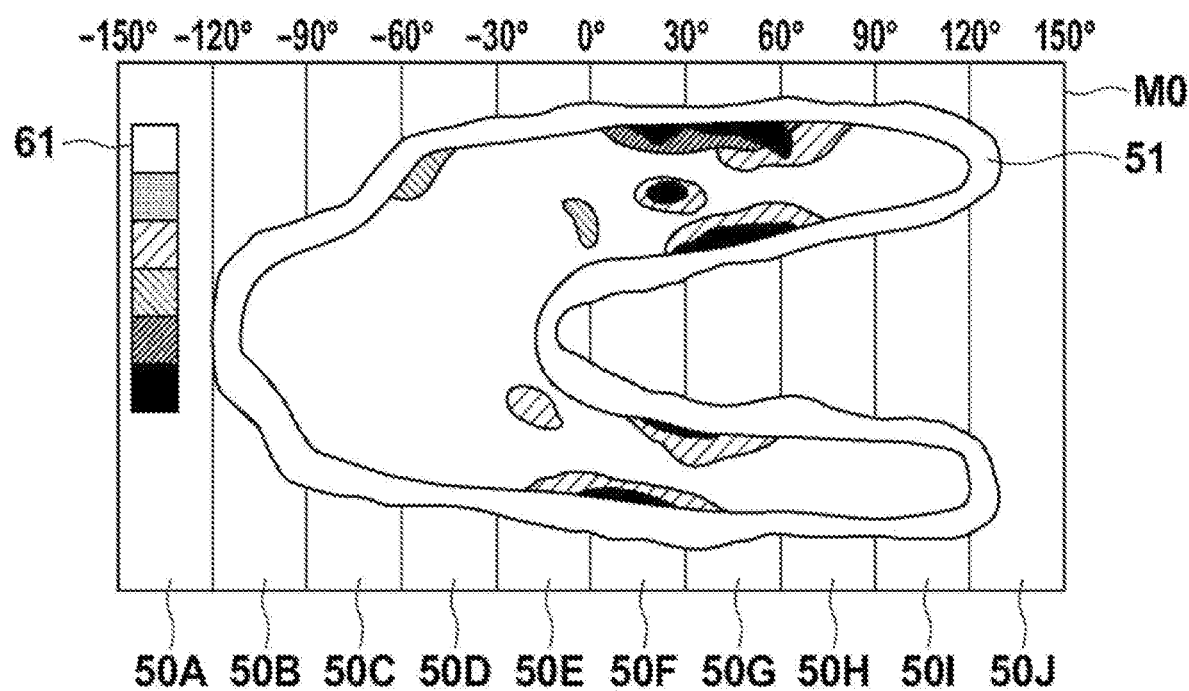
FIG. 16 is a diagram illustrating a thickness map.

The quantification unit 24 generates a thickness map from the thickness of the cartilage region 51 at each position in the region of interest 52. FIG. 16 is a diagram illustrating a thickness map. As illustrated in FIG. 16, a thickness map M0 shows the thickness distribution of the cartilage region 51 in the region of interest 52 in colors in six scales. In the thickness map M0, as the color is darker, the cartilage region 51 is thinner. In FIG. 16, different colors are represented by differences in the hatching. The thickness map M0 includes a reference 61 that indicates the relationships between the colors and the thickness. With reference to the reference 61, the thickness distribution of the cartilage region 51 in the region of interest 52 can be easily recognized visually on the thickness map M0.

The quantification unit 24 may derive a quantitative value by using only a pixel position at which the thickness of the cartilage region 51 is greater than or equal to a threshold value in the unfolded image 50. For example, the quantification unit 24 may derive a quantitative value by using a pixel position at which the thickness of the cartilage region 51 is greater than or equal to 0.5 mm in the unfolded image 50. In this case, a pixel position at which the thickness of the cartilage is less than 0.5 mm is excluded from derivation of the quantitative value. Accordingly, a region in which the thickness is thin and which does not function as cartilage can be excluded from derivation of the quantitative value. In a case of deriving the defect area as a quantitative value, the quantification unit 24 needs to derive the defect area while assuming a pixel position at which the thickness of the cartilage is less than 0.5 mm as a pixel position at which cartilage is in defect.

The derived quantitative values as well as information including the patient's name, the imaging date and time, the position of the region of interest 52, and the unfolded image 50 are transmitted to and saved in the image storage server 3 in association with the three-dimensional image G0.

The display control unit 25 displays the thickness map M0 on the display unit 14.

Figure 17:
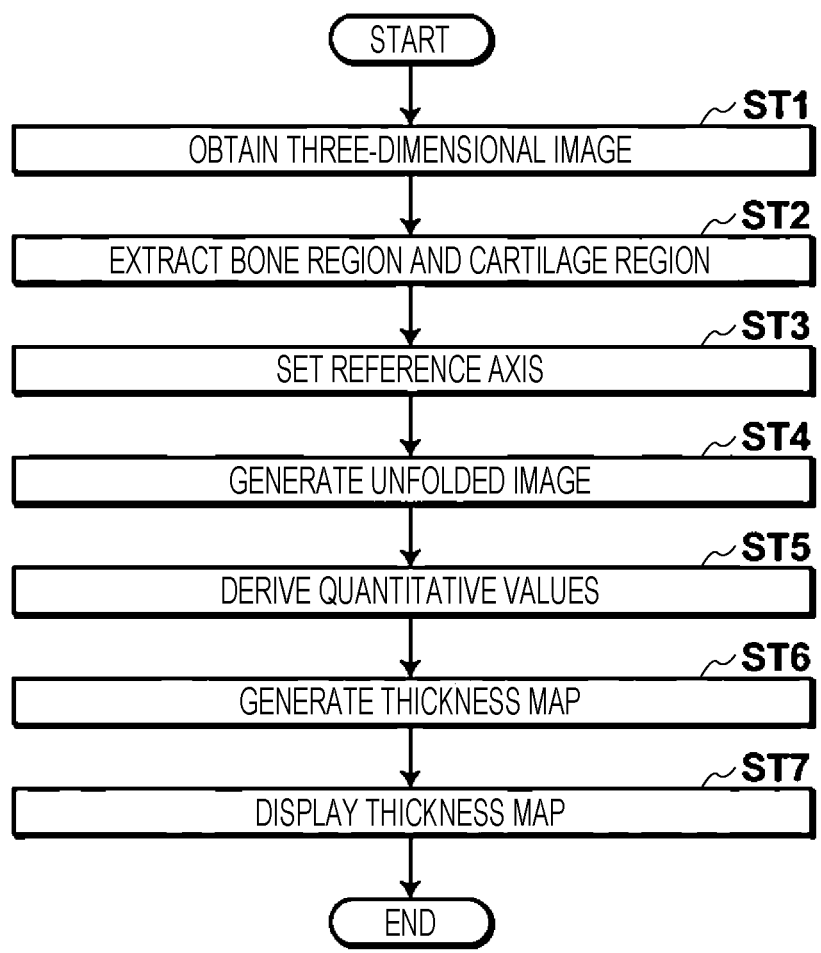
FIG. 17 is a flowchart illustrating a process performed in the first embodiment.

Now, a process performed in the first embodiment is described. FIG. 17 is a flowchart illustrating the process performed in the first embodiment. First, the image obtaining unit 21 obtains the three-dimensional image G0 (step ST1) and extracts a bone region and a cartilage region from the three-dimensional image G0 (step ST2). Next, the reference axis setting unit 22 sets, on the respective side surfaces of the joint of the femur 30, center positions determined on the basis of the anatomical characteristics of the joint and sets an axis that connects the center positions as the reference axis 46 (step ST3).

Next, the unfolding unit 23 unfolds the cartilage 32 included in the three-dimensional image G0 with reference to the reference axis 46 set by the reference axis setting unit 22 to generate the unfolded image 50 (step ST4). The quantification unit 24 derives quantitative values of the cartilage region 51 on the unfolded image 50 (step ST5) and generates the thickness map M0 from the derived quantitative values (step ST6). The display control unit 25 displays the thickness map M0 on the display unit 14 (step ST7), and the process ends.

Accordingly, in this embodiment, the cartilage 32 included in the three-dimensional image G0 is unfolded with reference to the reference axis 46, which is a specific axis in the joint, to generate the unfolded image 50. Therefore, on the unfolded image 50, partial regions of the joint do not overlap, and information regarding the cartilage on the joint surface can be checked with high accuracy. In a case where a projection image of the cartilage is used, to check the entire region of the cartilage in the joint, an operation for, for example, rotating the projection image needs to be performed. The condition of the cartilage on the entire surface of the joint can be easily checked by viewing the unfolded image 50 generated in this embodiment without an operation of, for example, rotation.

Figure 18:
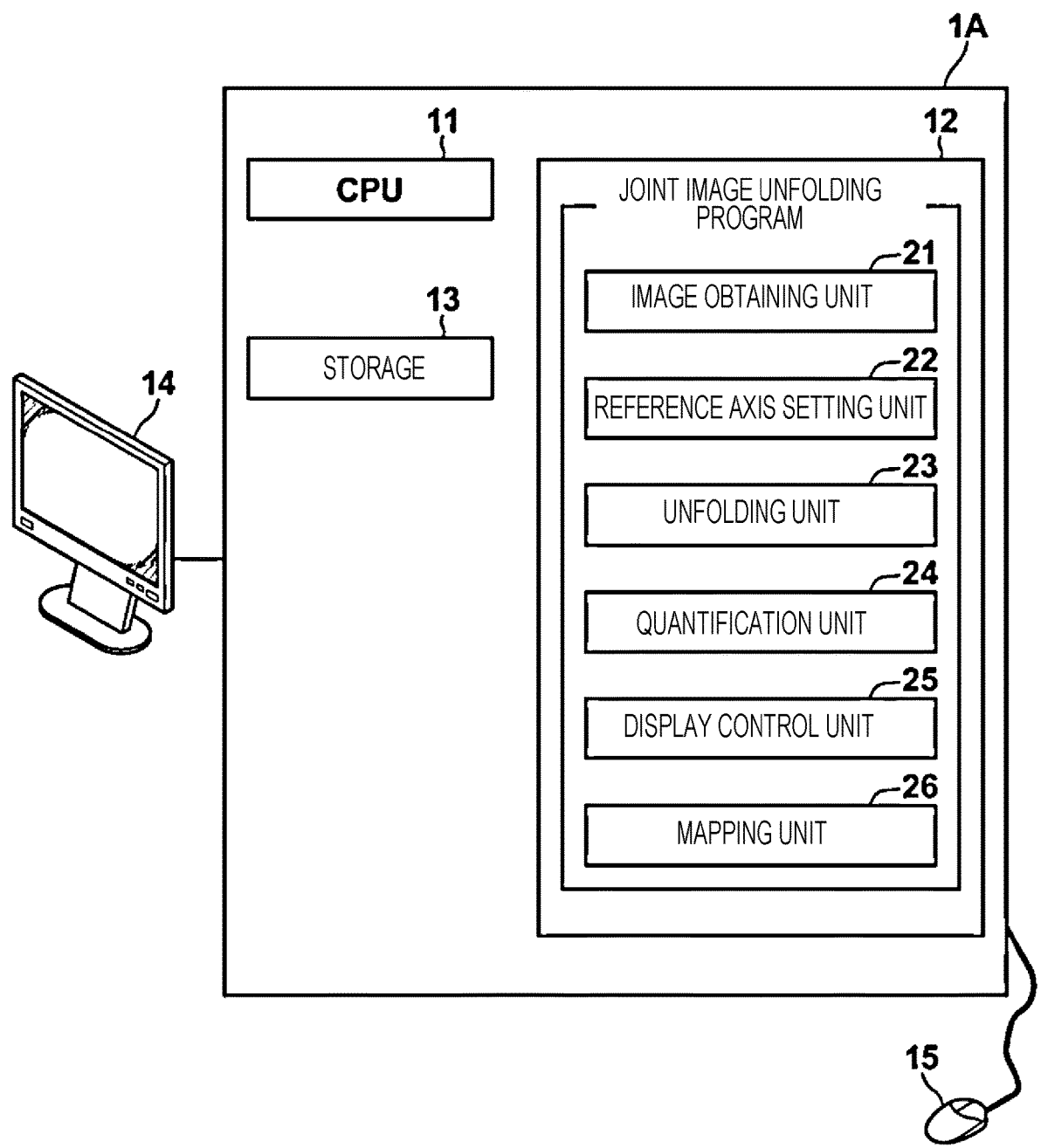
FIG. 18 is a schematic block diagram illustrating a configuration of a joint image unfolding apparatus according to a second embodiment.

Now, a second embodiment of the present disclosure is described. FIG. 18 is a diagram schematically illustrating a configuration of a joint image unfolding apparatus according to the second embodiment of the present disclosure. In FIG. 18, a component the same as that in FIG. 2 is assigned the same reference numeral, and a detailed description thereof is omitted. As illustrated in FIG. 18, a joint image unfolding apparatus 1A according to the second embodiment is different from that of the first embodiment in that the joint image unfolding apparatus 1A further includes a mapping unit 26 that generates a mapping image obtained by mapping a functional image of a joint onto an unfolded image. In FIG. 18, although the joint image unfolding apparatus 1A includes the quantification unit 24, the joint image unfolding apparatus 1A according to the second embodiment need not include the quantification unit 24.

In the second embodiment, the image obtaining unit 21 obtains a functional image F0 of the knee joint in addition to the three-dimensional image G0. In the second embodiment, as the functional image F0, a T2 map image is used. The T2 map image is one type of MRI image and represents a correlation with water in the knee joint as a signal value. In the T2 map image, for example, as the correlation with water is higher, the signal value at each pixel is larger.

In the second embodiment, also for the functional image F0, the unfolding unit 23 generates an unfolded image with reference to the reference axis 46 set by the reference axis setting unit 22 as in the first embodiment. The unfolded image of the functional image F0 is referred to as a functional unfolded image 70. The cartilage 32 of the femur 30 has a thickness, and therefore, in the functional image F0, the signal value differs in the thickness direction of the cartilage 32. In the second embodiment, the unfolding unit 23 sets an intermediate plane in the thickness direction of the cartilage 32 and deploys the signal values of the functional image F0 in the intermediate plane to generate the functional unfolded image 70. The unfolding unit 23 may generate the functional unfolded image 70 by using a representative value, such as the average value, the maximum value, the minimum value, or the intermediate value, of the signal value in the thickness direction of the cartilage 32.

Here, although the part included in the three-dimensional image G0 and the functional image F0 is the same knee joint, the imaging times are different. Therefore, the mapping unit 26 registers the unfolded image 50 and the functional unfolded image 70. As the method for registration, any known method, such as rigid registration or non-rigid registration, can be used. The mapping unit 26 may perform registration by transforming the unfolded image 50 so as to be aligned with the functional unfolded image 70 or may perform registration by transforming the functional unfolded image 70 so as to be aligned with the unfolded image 50. The mapping unit 26 generates a mapping image M1 obtained by mapping the functional unfolded image 70 onto the unfolded image 50.

Figure 19:
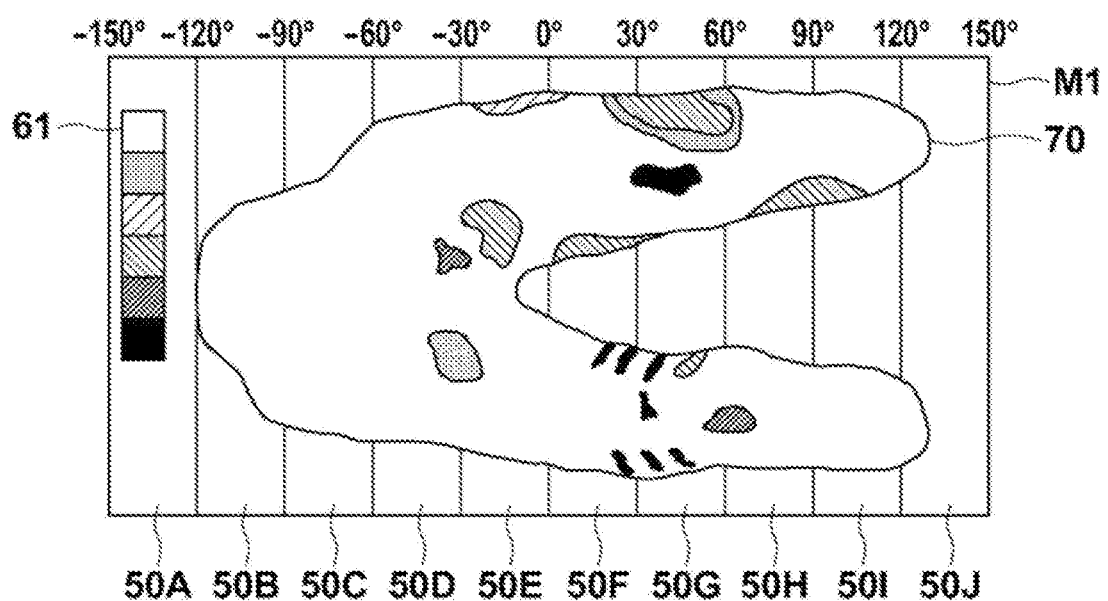
FIG. 19 is a diagram illustrating a mapping image.

FIG. 19 is a diagram illustrating the mapping image M1. As illustrated in FIG. 19, the mapping image M1 shows the magnitude of the correlation with water in the cartilage 32 of the femur 30 in colors in six scales. In the mapping image M1, as the color is darker, the correlation with water is lower. In FIG. 19, different colors are represented by differences in the hatching. The mapping image M1 includes a reference 62 that indicates the relationships between the colors and the correlation with water. With reference to the reference 62, the correlation of the cartilage 32 with water can be easily recognized visually. Although the region of interest 52 is not set in the mapping image M1 illustrated in FIG. 19, the region of interest 52 may be set as in the first embodiment and the mapping image M1 may be generated only for the region of interest 52.

Figure 20:
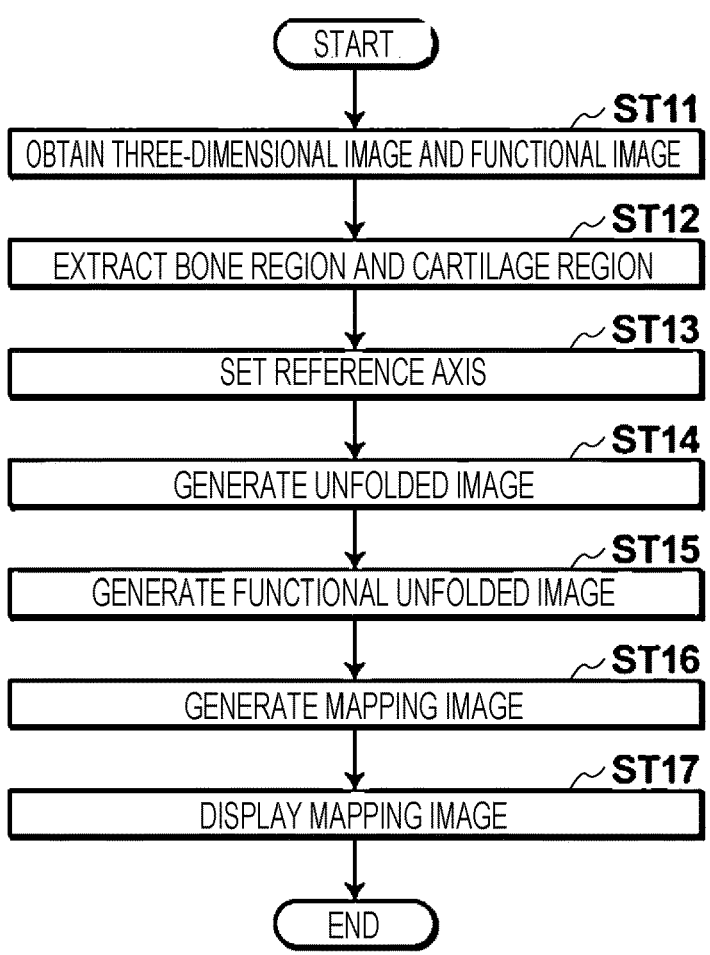
FIG. 20 is a flowchart illustrating a process performed in the second embodiment.

Now, a process performed in the second embodiment is described. FIG. 20 is a flowchart illustrating the process performed in the second embodiment. First, the image obtaining unit 21 obtains the three-dimensional image G0 and the functional image F0 (step ST11) and extracts a bone region and a cartilage region from the three-dimensional image G0 (step ST12). Next, the reference axis setting unit 22 sets, on the respective side surfaces of the joint of the femur 30, center positions determined on the basis of the anatomical characteristics of the joint and sets an axis that connects the center positions as the reference axis 46 (step ST13).

Next, the unfolding unit 23 unfolds the cartilage 32 included in the three-dimensional image G0 with reference to the reference axis 46 set by the reference axis setting unit 22 to generate the unfolded image 50 (step ST14). The unfolding unit 23 unfolds the functional image F0 with reference to the reference axis 46 set by the reference axis setting unit 22 to generate the functional unfolded image 70 (step ST15). The mapping unit 26 generates the mapping image M1 obtained by mapping the functional unfolded image 70 onto the unfolded image 50 (step ST16). The display control unit 25 displays the mapping image M1 on the display unit 14 (step ST17), and the process ends.

Now, a third embodiment of the present disclosure is described. Note that the configuration of a joint image unfolding apparatus according to the third embodiment is the same as those of the joint image unfolding apparatuses according to the first and second embodiments described above and only a process to be performed is different, and therefore, a detailed description of the apparatus is omitted here. The joint image unfolding apparatus according to the third embodiment is different from those of the first and second embodiments in that the display control unit 25 displays the unfolded image 50 generated by the unfolding unit 23 on the display unit 14.

Figure 21:
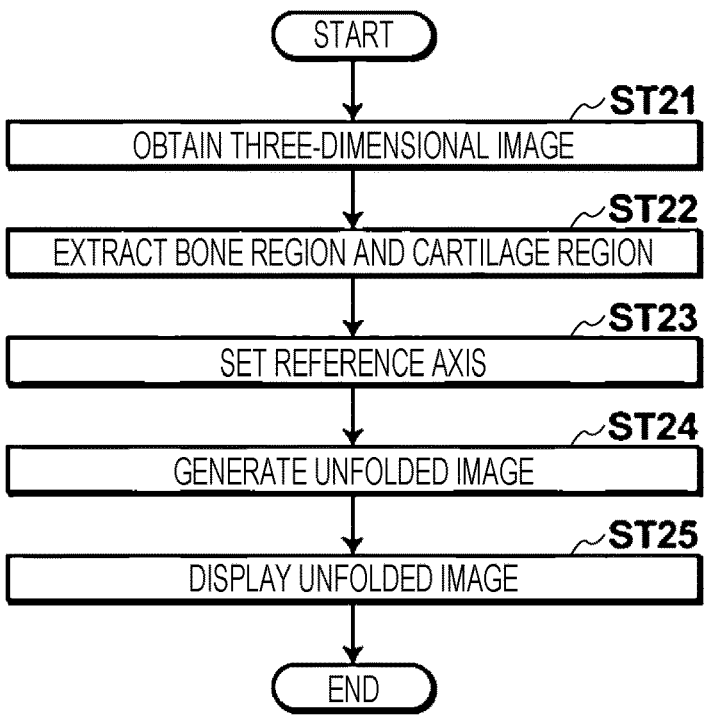
FIG. 21 is a flowchart illustrating a process performed in a third embodiment.

Now, the process performed in the third embodiment is described. FIG. 21 is a flowchart illustrating the process performed in the third embodiment. First, the image obtaining unit 21 obtains the three-dimensional image G0 (step ST21) and extracts a bone region and a cartilage region from the three-dimensional image G0 (step ST22). Next, the reference axis setting unit 22 sets, on the respective side surfaces of the joint of the femur 30, center positions determined on the basis of the anatomical characteristics of the joint and sets an axis that connects the center positions as the reference axis 46 (step ST23).

Next, the unfolding unit 23 unfolds the cartilage 32 included in the three-dimensional image G0 with reference to the reference axis 46 set by the reference axis setting unit 22 to generate the unfolded image 50 (step ST24). The display control unit 25 displays the unfolded image 50 on the display unit 14 (step ST25), and the process ends.

Figure 22:
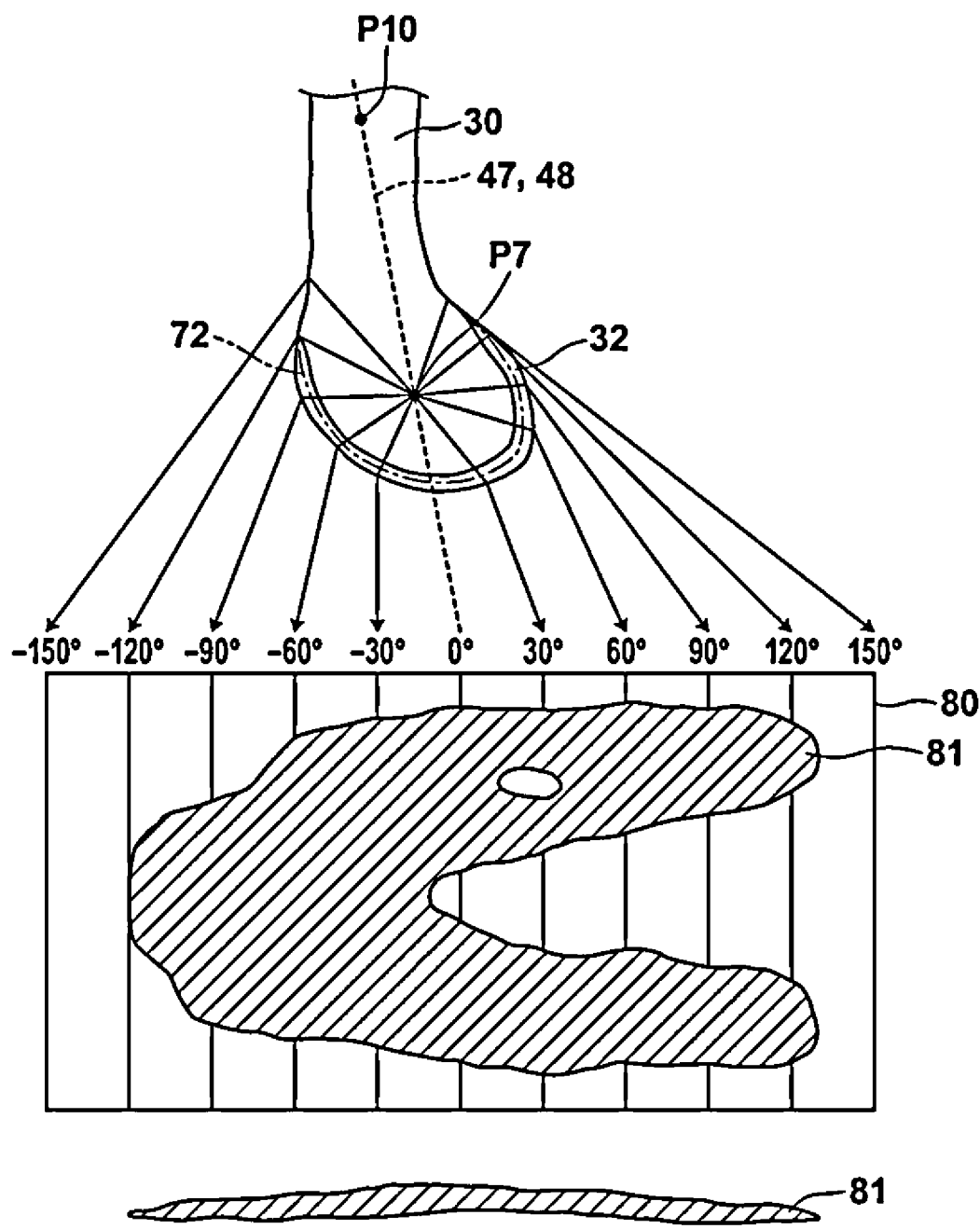
FIG. 22 is a diagram for explaining generation of a three-dimensional unfolded image in a fourth embodiment.
Figure 23:
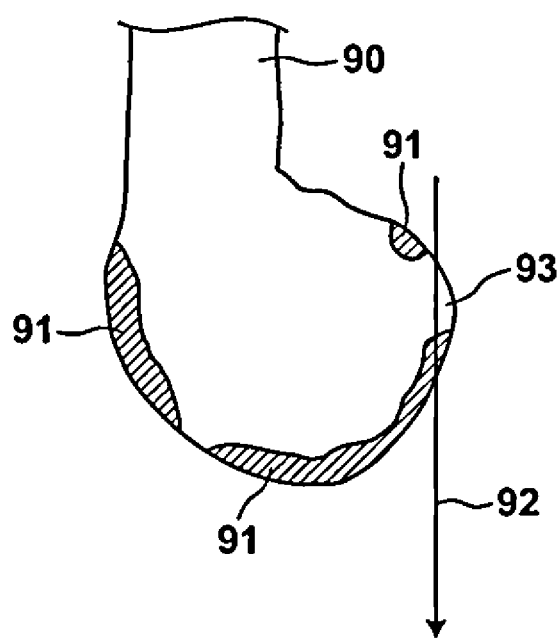
FIG. 23 is a diagram for explaining generation of a projection image of cartilage.

Now, a fourth embodiment of the present disclosure is described. In the first to third embodiments described above, the unfolded image 50, which is a two-dimensional image, is generated. The fourth embodiment is different from the first to third embodiments in that a three-dimensional unfolded image is generated. FIG. 22 is a diagram for explaining generation of a three-dimensional unfolded image in the fourth embodiment. As illustrated in FIG. 22, the cartilage 32 having a certain thickness is present in the joint of the femur 30. The unfolding unit 23 obtains the center position in the thickness direction of the cartilage 32 in each radial direction from the reference axis 46, which is the center, as illustrated in FIG. 13. In FIG. 22, a line that connects the center positions in the thickness direction of the cartilage 32 is illustrated as a center line 72.

The unfolding unit 23 unfolds, for each local position on the reference axis 46 and with reference to the reference axis 46, the cartilage 32 of the femur 30 along the center line 72 onto a plane to generate a three-dimensional unfolded image 80. The three-dimensional unfolded image 80 includes a three-dimensional cartilage region 81. As in the first embodiment, a region of interest may be set in the cartilage region 81. In FIG. 22, the unfolded image 80 shows angles with respect to the reference axis 46 as in FIG. 13. FIG. 22 includes a plan view of the unfolded image 80 and a side view of the cartilage region 81 when viewed in the first direction of the femur 30.

Also for the three-dimensional unfolded image 80 thus generated, quantitative values can be derived to generate the thickness map M0 as described above. As in the second embodiment, the mapping image M1 obtained by superimposing the functional image F0 on the three-dimensional unfolded image 80 can be generated. As in the third embodiment, the three-dimensional unfolded image 80 can be displayed on the display unit 14 by, for example, volume rendering display.

There is a case where a plurality of three-dimensional images of the same subject captured at different times are compared with each other for a follow-up. In such a case, in a case where an unfolded image is generated for a first three-dimensional image G1 captured in the past, it is preferable to generate an unfolded image also for a newly captured second three-dimensional image G2 for a follow-up. The first three-dimensional image G1 corresponds to another three-dimensional image of the present disclosure. In this case, although the cartilage may be worn over time, the joint is not deformed. Therefore, it is preferable that when an unfolded image is generated for the first three-dimensional image G1, information indicating the position of the reference axis be saved in the image storage server 3, and when an unfolded image of the second three-dimensional image G2 is generated, the saved information regarding the reference axis of the same subject be obtained to generate the unfolded image by using the obtained information regarding the reference axis.

Accordingly, the computational load for generating the unfolded image of the second three-dimensional image G2 can be reduced. In this case, in a case where the region of interest 52 is set for the unfolded image of the first three-dimensional image G1, it is preferable to set, for the unfolded image of the second three-dimensional image G2, a region of interest the same as that of the unfolded image of the first three-dimensional image G1. Accordingly, the state of the cartilage in the first three-dimensional image G1 and the state of the cartilage in the second three-dimensional image G2 can be easily compared with each other.

When unfolded images are generated from the three-dimensional images G0 of a plurality of different subjects, the same reference axis may be set. In this case, it is preferable to make the reference positions for generating the unfolded images be the same for the three-dimensional images G0 of the plurality of different subjects. Accordingly, in the unfolded images of cartilages, of the respective subjects, having different forms, the positions of the joints can be aligned. As a result, the states of the cartilages of the subjects can be easily compared with each other.

In the embodiments described above, although the unfolded image is divided into a plurality of regions on the basis of the angle in increments of 30 degrees, the number of divided regions is not limited to this. The unfolded image may be divided on the basis of the angle in increments of a smaller degree or in increments of a larger degree. Quantitative values may be derived for the entire region of interest 52 without dividing the unfolded image into regions. The unfolded image may be displayed on the display unit 14 to allow an operator to specify the region of interest 52.

In the embodiments described above, although quantitative values are derived for the region of interest 52 included in the unfolded image 50, quantitative values may be derived for the entire cartilage region 51 included in the unfolded image 50 without setting the region of interest 52.

In the embodiments described above, the area of the cartilage region 51, the area of the cartilage region 51 in the region of interest 52, the thickness of the cartilage region 51, the volume of the cartilage region 51, the cover ratio of the cartilage region 51 in the region of interest 52, the defect area of the cartilage region 51 in the region of interest 52, and a representative value of the thickness of the cartilage region 51 at each position in the region of interest 52 are derived as quantitative values; however, any one of these quantitative values or any combination of the quantitative values may be derived.

In the embodiments described above, although quantitative values of the cartilage of the knee joint are derived, the present disclosure is not limited to this. The present disclosure can be provided when quantitative values of cartilage of, for example, an elbow joint, a hip joint, a shoulder joint, or an intervertebral joint are derived.

In the embodiments described above, as the hardware configuration of the processing units that perform various processes, namely, for example, the image obtaining unit 21, the reference axis setting unit 22, the unfolding unit 23, the quantification unit 24, the display control unit 25, and the mapping unit 26, various processors described below can be used. The various processors include, as described above, a CPU (central processing unit), which is a general-purpose processor executing software (program) to function as various processing units, a programmable logic device (PLD), such as an FPGA (field-programmable gate array), which is a processor having a circuit configuration that is changeable after manufacture, and a dedicated electric circuit, such as an ASIC (application-specific integrated circuit), which is a processor having a circuit configuration specifically designed to perform a specific process.

One processing unit may be configured as one of the various processors or a combination of two or more processors of the same type or different types (for example, a combination of a plurality of FPGAs or a combination of a CPU and an FPGA). Further, a plurality of processing units may be configured as one processor.

As the first example of configuring a plurality of processing units as one processor, a form is possible where one or more CPUs and software are combined to configure one processor, and the processor functions as the plurality of processing units, representative examples of which are computers including a client and a server. As the second example thereof, a form is possible where a processor is used in which the functions of the entire system including the plurality of processing units are implemented as one IC (integrated circuit) chip, a representative example of which is a system on chip (SoC). As described above, as the hardware configuration, the various processing units are configured by using one or more of the various processors described above.

Further, as the hardware configuration of the various processors, more specifically, an electric circuit (circuitry) in which circuit elements, such as semiconductor elements, are combined can be used.

REFERENCE SIGNS LIST 1, 1A joint image unfolding apparatus
2 three-dimensional imaging apparatus
3 image storage server
4 network
11 CPU
12 memory
13 storage
14 display unit
15 input unit
21 image obtaining unit
22 reference axis setting unit
23 unfolding unit
24 quantification unit
25 display control unit
26 mapping unit
30 femur
30A cut femur
31 tibia
32, 33 cartilage
34 menisci
35 medial condyle
36 lateral condyle
37 section
40, 41, 48 plane
42 major axis
43 minor axis
44, 45 ellipse
46 reference axis
47 anatomical axis
50 unfolded image
50A to 50J region
51 cartilage region
52 region of interest
53 defect region
60 projecting part 61, 62 reference
70 functional unfolded image
72 center line
80 three-dimensional unfolded image
81 three-dimensional cartilage region
F0 functional image
G0, G1, G2 three-dimensional image
M0 thickness map
M1 mapping image
P1 to P5 point
P6 position
P7 to P10 center position

What is claimed is:

1. A joint image unfolding apparatus comprising:
at least one processor configured to:
obtain a three-dimensional image of a joint having cartilage,
set, on respective side surfaces of the joint, center positions along a latitudinal direction determined on the basis of an anatomical characteristic of the joint and set an axis that connects the center positions as a reference axis, wherein each of the center positions is a center of an ellipse;
set an anatomical axis along a longitudinal direction that passes through a first center position of the reference axis and a second center position of the joint which is a predetermined distance away from the reference axis along the longitudinal direction;
set a reference plane to coincide with the reference axis and the anatomical axis; and
generate an unfolded image with reference to the reference plane and the reference axis, wherein an angle with respect to the anatomical axis corresponding to a reference position is set to 0 degree for the reference plane.

2. The joint image unfolding apparatus according to claim 1, wherein the processor sets the anatomical axis that passes through a third center position of the reference axis and a reference point set on a side opposite to a joint surface across the third center position of the reference axis and generates the unfolded image with reference to a plane passing though the reference axis and the anatomical axis.

3. The joint image unfolding apparatus according to claim 1, wherein the processor is further configured to derive a quantitative value of the cartilage on the unfolded image.

4. The joint image unfolding apparatus according to claim 3, wherein the processor derives the quantitative value for a region of interest on the unfolded image.

5. The joint image unfolding apparatus according to claim 4, wherein the processor sets the region of interest on the basis of a contour that defines a region in which the cartilage is to be present in the joint.

6. The joint image unfolding apparatus according to claim 4, wherein the processor derives a cover ratio of the cartilage in the region of interest as the quantitative value.

7. The joint image unfolding apparatus according to claim 4, wherein the processor derives a defect area of the cartilage in the region of interest as the quantitative value.

8. The joint image unfolding apparatus according to claim 4, wherein the processor derives a thickness of the cartilage at each position in the region of interest as the quantitative value.

9. The joint image unfolding apparatus according to claim 8, wherein the processor generates a thickness map of the cartilage in the region of interest.

10. The joint image unfolding apparatus according to claim 4, wherein the processor derives the quantitative value only for a region in which a thickness of the cartilage in the region of interest is greater than or equal to a predetermined threshold value.

11. The joint image unfolding apparatus according to claim 4, wherein the processor divides the region of interest on the unfolded image into regions and derives the quantitative value for each of the regions obtained as a result of division.

12. The joint image unfolding apparatus according to claim 4, wherein in a case where a result of deriving another quantitative value derived from another three-dimensional image of a subject the same as a subject for which the three-dimensional image is obtained is present, the other three-dimensional image being captured at a different time from a time when the three-dimensional image is captured, the processor sets the region of interest at a position the same as a position of a region of interest for which the other quantitative value is derived.

13. The joint image unfolding apparatus according to claim 3, wherein the processor derives an area of the cartilage on the unfolded image as the quantitative value.

14. The joint image unfolding apparatus according to claim 3, wherein the processor derives a volume of the cartilage on the unfolded image as the quantitative value.

15. The joint image unfolding apparatus according to claim 1, wherein in a case where another unfolded image generated from another three-dimensional image of a subject the same as a subject for which the three-dimensional image is obtained is present, the other three-dimensional image being captured at a different time from a time when the three-dimensional image is captured, the processor generates the unfolded image with reference to the reference axis the same as a reference axis with reference to which the other unfolded image is generated.

16. The joint image unfolding apparatus according to claim 1, wherein the processor is further configured to generate a mapping image obtained by mapping a functional image of the joint onto the unfolded image.

17. The joint image unfolding apparatus according to claim 1, wherein the joint is a knee joint, an elbow joint, a hip joint, a shoulder joint, or an intervertebral joint.

18. The joint image unfolding apparatus according to claim 1, wherein the first center position is a central position between a first center of the ellipse on a first side of the side surfaces of the joint and a second center of the ellipse on a second side of the side surfaces of the joint, the second side is opposite to the first side, and the second center position is a center of a fitted ellipse.

19. A joint image unfolding method comprising:
obtaining a three-dimensional image of a joint having cartilage;
setting, on respective side surfaces of the joint, center positions determined on the basis of an anatomical characteristic of the joint and set an axis that connects the center positions along a latitudinal direction as a reference axis, wherein each of the center positions is a center of an ellipse;
setting an anatomical axis along a longitudinal direction that passes through a first center position of the reference axis and a second center position of the joint which is a predetermined distance away from the reference axis along the longitudinal direction;
setting a reference plane to coincide with the reference axis and the anatomical axis; and
generating an unfolded image with reference to the reference plane and the reference axis, wherein an angle with respect to the anatomical axis corresponding to a reference position is set to 0 degree for the reference plane.

20. A non-transitory computer readable recording medium storing a joint image unfolding program for causing a computer to perform a procedure comprising:

obtaining a three-dimensional image of a joint having cartilage;

setting, on respective side surfaces of the joint, center positions along a latitudinal direction determined on the basis of an anatomical characteristic of the joint and set an axis that connects the center positions as a reference axis, wherein each of the center positions is a center of an ellipse;

setting an anatomical axis along a longitudinal direction that passes through a first center position of the reference axis and a second center position of the joint which is a predetermined distance away from the reference axis along the longitudinal direction;

setting a reference plane to coincide with the reference axis and the anatomical axis; and generating an unfolded image with reference to the reference plane and the reference axis, wherein an angle with respect to the anatomical axis corresponding to a reference position is set to 0 degree for the reference plane.

* * * * *